United States Patent [19]

Hibino et al.

[11] Patent Number: 4,803,287

[45] Date of Patent: Feb. 7, 1989

[54] CERTAIN PHOTOCHROMIC FULGIDE COMPOUNDS AND METHOD FOR THEIR SYNTHESIS

[75] Inventors: Junichi Hibino, Kyoto; Eiji Ando, Katano, both of Japan

[73] Assignee: Director-General of the Agency of Industrial Science and Technology, Tokyo, Japan

[21] Appl. No.: 23,253

[22] Filed: Mar. 9, 1987

[30] Foreign Application Priority Data

Apr. 16, 1986 [JP] Japan .................................. 61-86188
Jul. 3, 1986 [JP] Japan ................................. 61-155113
Oct. 17, 1986 [JP] Japan ................................. 61-245363
Oct. 17, 1986 [JP] Japan ................................. 61-245364

[51] Int. Cl.$^4$ .......................................... C07D 307/60
[52] U.S. Cl. ................................... 549/252; 549/483; 430/343
[58] Field of Search ......................................... 549/252

[56] References Cited

U.S. PATENT DOCUMENTS 4,220,708 9/1980 Heller et al. ......................... 549/58

OTHER PUBLICATIONS

Heller et al., J. C. S. Perkin I, pp. 197–201 (1981).

Primary Examiner—John M. Ford
Assistant Examiner—Bernard I. Dentz
Attorney, Agent, or Firm—Stevens, Davis, Miller & Mosher

[57] ABSTRACT

The invention provides a photochromic material characterized by an improvement in balance of the substituents in the conventional furylfulgides and represented by the general formula:

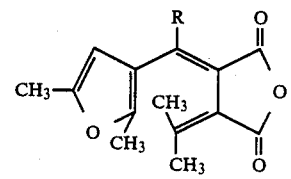

(wherein R represents an alkyl chain having 5 to 31 carbon atoms). According to this molecular structure, a mutually appropriate steric hindrance is induced between the isopropylidene group and the long-chain alkyl group to make the regio isomer unstable, thus preventing the regio isomer from being by-produced while also inhibiting any isomerization reaction from occuring in the synthesis of the fulgide. Further, a good balance of hydrophilic part and hydrophobic part is produced to facilitate formation of a Langmuir-Blodgett film.

4 Claims, No Drawings

CERTAIN PHOTOCHROMIC FULGIDE COMPOUNDS AND METHOD FOR THEIR SYNTHESIS

BACKGROUND OF THE INVENTION

This invention relates to an optical recording medium for making optical read and write of information by using an organic dye.

Photochromic materials are attracting attention for their availability for the erasable optical recording media owing to their specific property that they undergo a reversible change of color upon exposure to two types of light source differing in wavelength. Fulgides are known as a typical example of such photochromic materials. Fulgides are compounds having an alkylidene group bonded to each of the two methylene carbons of succinic anhydride or succinic imide thereof, and represented by the following general formula (1):

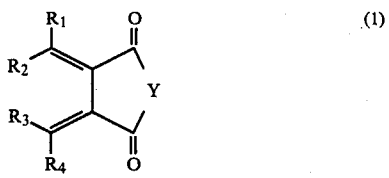

(wherein at least one of $R_2$ and $R_3$ represents an aromatic ring, and Y represents O or

A large number of fulgide compounds have been known up to date. Among them, fulgide (2) is one of the fulgides having the most excellent photochromic properties (JCS Perkin Trans. I, 202, (1981)). This fulgide (2), when irradiated with ultraviolet light of 337 nm, is ring closed and converted into the red benzofuran form (3), but when the latter is irradiated with visible light of 473 nm, it returns to fulgide (2).

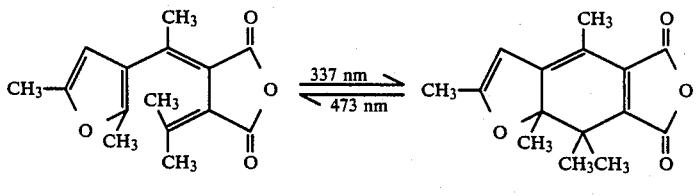

There are two problems in utilization of fulgide (2) for an optical recording medium. One problem is the presence of the regio isomer (4) which has no action of inducing photochromic reaction. Thus, the incidental formation of regio isomer (4) in the synthesis of fulgide (2) and the lowering of conversion rate of the principal reaction due to the side reaction of forming regio isomer (4) in the step of ultraviolet-light irradiation of fulgide (2) have been the pending questions.

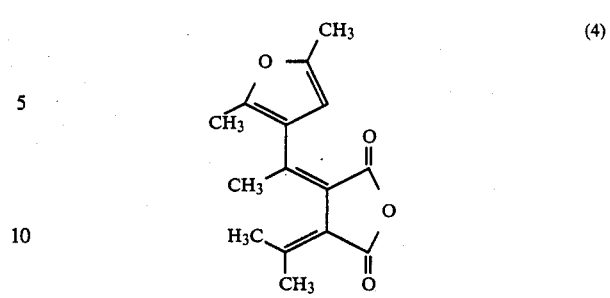

In utilization of photochromic compounds for optical recording media, light quantum detector elements, etc., it is required to reduce the film thickness in correspondence to the miniaturization in size of electronic parts. Another problem is the impossibility to attain the desired thin films of fulgides by the Langumuir-Blodgett technique, which is an excellent method to produce ultra-thin organic films. For forming Langmuir-Blodgett films, it is necessary that a hydrophobic group (for example, hydrocarbon chain) and a hydrophilic group (for example, carbonyl group) be contained in a molecule. Since the introduction of a hydrophobic group into the molecule of fulgide (2) is attended with difficulties in the synthesis thereof, no successful attempt of such introduction has been reported.

SUMMARY OF THE INVENTION

The present invention has for its object to prevent any regio isomer from being by-produced while also inhibiting the side reaction of forming such regio isomer from occuring in the synthesis of fulgide by unstabilizing the regio isomer in the fulgide and to form a thin film by using the Langmuir-Blodgett method to afford the photochromism of fulgide to the thin film. For attaining this object, the invention relates to a fulgide. The fulgide provided according to this invention is characterized in that methyl is selected as Rb and Rc and an alkyl chain having 5 to 31 carbon atoms as Ra in the following formula:

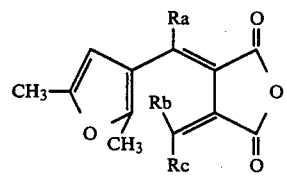

This molecular structure causes a mutually appropriate steric hindrance between the isopropylidene group and the long-chain alkyl group, and such steric hindrance contributes to unstabilizing the regio isomer to prevent the regio isomer from being by-produced while also inhibiting the isomerization reaction from occuring in the synthesis of fulgide. Further, the hydrophilicity of pigment skeleton and the hydrophobicity of alkyl chain are well-balanced to facilitate the formation of the Langmuir-Blodgett film.

BRIEF DESCRIPTION OF THE DRAWINGS

FIG. 1 shows the ultraviolet visible absorption spectra in chloroform of the fulgide (FF-10) used in the Examples of this invention and its colored form. In FIG. 1, curve A shows the ultraviolet visible absorption spectrum of a chloroform solution of FF-10, and curve B shows the ultraviolet visible absorption spectrum of the chloroform solution of FF-10 which has been irradiated with ultraviolet light and colored in red.

FIG. 2 shows the ultraviolet visible absorption spectra on a Langmuir-Blodgett film of the fulgide (FF-10) used in the Examples of this invention and its colored form. Curve A shows the absorption spectrum before ultraviolet-light irradiation and curve B shows the absorption spectrum after ultraviolet-light irradiation.

DETAILED DESCRIPTION OF THE INVENTION

The invention will hereinafter be described more in detail with reference to the examples thereof.

EXAMPLE 1

The fulgide used in this example (hereinafter referred to as FF-10) has the following chemical structure:

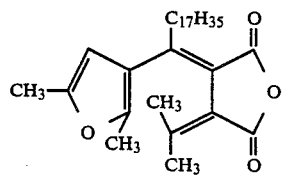

First, the process for synthesizing the intermediate ketofuran is described. In the production of fulgides in the prior art, an acid anhydride (acetic anhydride) has been used since the intermediate ketofuran was acetylfuran in all cases. It is however difficult to obtain an acid anhydride containing long chains, so that in the examples of this invention an acid chloride was used in place of the acid anhydride.

(a) To a benzene solution containing 1 mol of 2,5-dimethylfuran and 1.5 mol of stearoyl chloride, another benzene solution containing 1 mol of anhydrous tin (IV) chloride was added at 0° C. over a period of one hour. The mixed solution was stirred for several hours and then poured into ice (1.5 kg) and 5M hydrochloric acid (500 ml). The inorganic layer was extracted with ethyl acetate and joined with the organic layer, and the joined layer was washed with water and, the solvent was removed by evaporation. The resulting product was recrystallized from methanol to obtain 0.8 mol of long-chain ketofuran to be used as the intermediate.

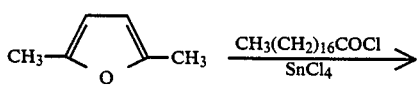

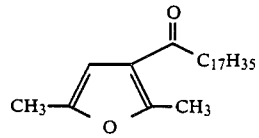

Next, the process for synthesizing FF-10 by using said intermediate ketofuran is described.

(b) Petroleum ether was added to 1 mol of sodium hydride, and the mixture was stirred for 5 minutes. Then the mixture was allowed to stand as it was, and after removing the supernatant, a mixture of 1.5 mol of acetone and 1 mol of diethyl succinate was added to the solution. The reaction started upon addition of one drop of ethanol to the mixture, and hydrogen was generated vigorously. After generation of hydrogen was ceased, diethyl ether was added and the reaction mixture was further stirred. One hour thereafter, the reaction mixture was diluted with ethyl acetate and extracted with 1M sodium carbonate. When the extract was acidified with care, the organic layer was separated out. This organic layer was extracted with ethyl acetate, dried over anhydrous magnesium sulfate, then, the solvent was removed by evaporation to obtain 0.8 mol of half ester.

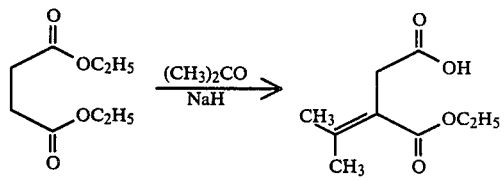

(c) The thus obtained 0.8 mol of half ester was dissolved in 500 ml of ethanol, and after adding 50 ml of concentrated sulfuric acid, the mixture was refluxed under heating. 3 hours thereafter, the mixture was concentrated by evaporating the solvent and the residue thus obtained was diluted with diethyl ether, then the diethylether solution was washed with a sodium hydrogen carbonate aqueous solution, again dried and concentrated. The resulting residue was purified by a column chromatography to obtain 0.8 mol of diester.

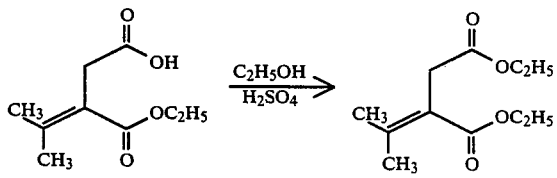

(d) In the prior art, potassium tert-butoxide has been used for the coupling reaction of diester and ketofuran. When this method was applied for the coupling reaction with said long-chain ketofuran, the reaction hardly proceeded. However, when potassium-tert-butoxide was replaced with strongly reactive sodium hydride, the reaction proceeded quickly. Petroleum ether was added to 1.2 mol of sodium hydride and the mixture was stirred for 5 minutes. Then the mixture was left still and the supernatant was removed. To the residue was added a mixture of 0.8 mol of long-chain ketofuran and 0.8 mol of the diester obtained in (b) described above, said mixture was dissolved in as small an amount of petroleum ether as possible. When one drop of ethanol was added to the mixture, then the reaction, was started, and hydrogen was generated vigorously. After generation of hydrogen was ceased, diethyl ether was added to the reaction mixture and stirred thereof was further continued. One hour thereafter, the reaction mixture was diluted with ethyl acetate and extracted with a 1M sodium carbonate solution. When the extract was acidified with care, and the organic layer was separated out. This organic layer was extracted with ethyl acetate, dried over anhydrous magnesium sulfate and, the solvent was removed by evaporation. The resulting residue was purified by a column chromatography to obtain 0.5 mol of half ester.

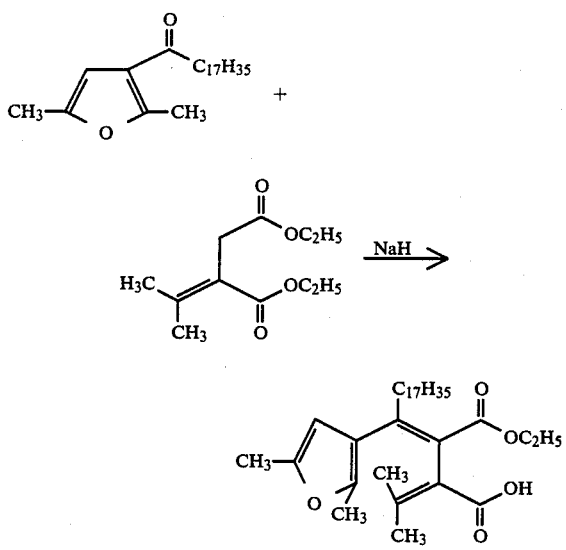

(e) The thus obtained 0.5 mol of half ester was dissolved in a 5% alcoholic potassium hydroxide solution and refluxed under heating for 15 hours. The resulting solution was poured into 6N hydrochloric acid and extracted with ethyl acetate, and the extract was dried over anhydrous sodium sulfate and, the solvent was removed by evaporation to obtain 0.3 mol of dicarboxylic acid. 100 Milliliters of acetyl chloride was added to this dicarboxylic acid and the mixture was stirred at room temperature for 10 minutes. Thereafter, the reaction mixture was concentrated by removing the solvent and the residue was purified by a silica gel column chromatography. For further raising the purity of the objective product, the reaction product was recrystallized from methanol to obtain 0.1 mol of the final objective product fulgide FF-10.

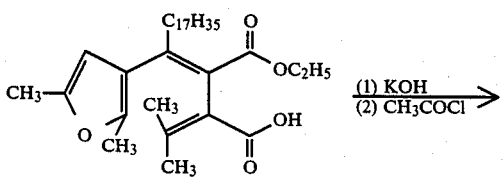

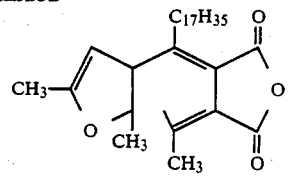

Liquid chromatography of the final product developed a single peak, but this peak perfectly disappeared upon ultraviolet-light irradiation and instead a peak corresponding to the benzofuran form appeared. No peak attributable to regio isomer was detected throughout this process. In the conventional synthetic process, the final product was obtained as a mixture of fulgide and its regio isomer, so that after running this step, an operation for separating them was necessary. According to the process of this invention, however, there was obtained the objective product FF-10 alone, and no regio isomer thereof was formed.

The ultraviolet visible absorption spectrum of a chloroform solution of FF-10 synthesized by the process described above is shown by curve A in FIG. 1. When this solution was irradiated with ultraviolet light of $\lambda = 344$ nm, there occurred ring closure of the fulgide and the solution assumed a red color. The ultraviolet visible absorption spectrum of this solution is shown by curve B in FIG. 1. When this solution was further irradiated with visible light of $\lambda = 500$ nm, ring opening of the fulgide took place and the solution lost its color and again became colorless. The solution, ether colorless or colored, was very stable in the dark place. No regio isomer was detected through the reaction process.

When fulgide was synthesized by the same process as described above except for use of hexanoyl chloride in place of stearoyl chloride in the step (a) and subjected to the same ultraviolet-light irradiation test, there was obtained the similar result (in case R was an alkyl chain having 5 carbon atoms). However, when fulgide was synthesized by using pentanoyl chloride in place of stearoyl chloride in said process, the produced fulgide had a regio isomer mixed therein (in case R was an alkyl chain having 4 carbon atoms).

The similar result was obtained with the fulgide synthesized from said process but by using dotriacontanoyl chloride in place of stearoyl chloride (in case R was an alkyl chain having 31 carbon atoms). However, for the compounds of longer chains, it was difficult to obtain the acid chloride to be used as starting material.

Thus, in accordance with the process of this invention, it is possible to obtain the objective fulgide in a high yield, without causing formation of regio isomer as the by-product, in case R is an alkyl chain having 5 to 31 carbon atoms.

EXAMPLE 2

A 0.3 mol toluene solution of FF-10 was spin coated on silica glass, which had been washed with trichloroethane, at 60 r.p.m. for 60 seconds to form a 1,000 Å thick recording layer. This recording layer was initially transparent, but when it was irradiated with ultraviolet light ($\lambda max = 366$ nm), a reaction took place rapidly in the recording layer to cause a change into colored FF-10, letting the recording layer assume a red color. Further irradiation thereof with visible light ($\lambda max = 500$ nm), however, caused quick restoration of the original form of FF-10 in the recording layer to make it transparent. No regio isomer was detected through this process.

EXAMPLE 3

By using a benzene solution of FF-10, a recording layer was formed on a substrate according to the Langmuir-Blodgett method under the following conditions:

Trough: 140 mm×600 mm
Subphase: pH 7.0; temp. 18° C.
Compression rate: 10 mm/min
Surface pressure: 15 mN/m
Deposition number of layers: 16

This recording layer was 300 Å in thickness, and it was a uniform ultra-thin film as compared with the recording layer obtained by spin coating in Example 2. In this recording layer, there occured the same reversible reactions as in the recording layer of Example 2 upon irradiation with two types of ultraviolet rays differing in wavelength. Also, no formation of regio isomer was observed through the process.

The best Langmuir-Blodgett film is formed when R is an alkyl chain having 17 carbon atoms. Also, in case R is an alkyl chain having 13 to 23 carbon atoms, good balance of hydrophilicity and hydrophobicity is provided and a relatively good Langmuir-Blodgett film can be obtained.

EXAMPLE 4

A benzene solution of a 1:2 mixture of FF-10 and octadecane was prepared, and a recording layer was formed by using this solution according to the process of Example 3. In this recording layer, there also took place the same reversible reactions as in the recording layer of Example 2 upon exposure to two types of light source differing in wavelength. The hydrocarbon (octadecane) used here gets in between the hydrophobic groups of FF-10 and serves for enhancing the stability of the film itself. Consequently, the half-life period of the colored version of this recording layer increased approximately 100 times that of the recoridng layer of Example 3.

The absorption spectra of this recording layer before and after ultraviolet-light irradiation are shown as curves A and B, respectively, in FIG. 2.

What is claimed is:

1. A photochromic material represented by the following general formula:

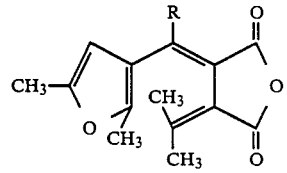

wherein R represents an alkyl chain having 13 to 31 carbon atoms.

2. A photochromic material according to claim 1, wherein R in the formula represents an alkyl chain having 13 to 23 carbon atoms.

3. A photochromic material according to claim 1, wherein R in the general formula represents an alkyl chain having 17 carbon atoms.

4. A process for preparing a photochromic compound of the formula:

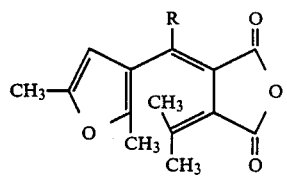

wherein R represents an alkyl chain having 13 to 31 carbon atoms which comprises condensing an intermediate for photochromic material represented by the following formula:

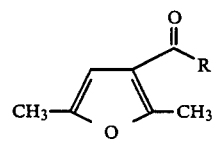

wherein R represents an alkyl chain having 13 to 31 carbon atoms, and a succinic acid derivative having an isopropylidene group represented by the following formula:

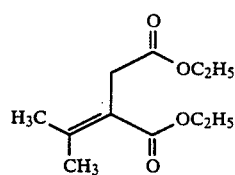

by the Stobbe condensation reaction, using sodium hydride as the basic compound; hydrolyzing the produced half ester to a dicarboxylic acid, and dehydrating said dicarboxylic acid.

* * * * *